(12) United States Patent
Wang et al.

(10) Patent No.: US 8,324,446 B2
(45) Date of Patent: Dec. 4, 2012

(54) UNITARY ABSORBENT CORE WITH BINDING AGENTS

(75) Inventors: James Hongxue Wang, Appleton, WI (US); Russell Paul George, Appleton, WI (US); Candace Dyan Krautkramer, Neenah, WI (US); Kenneth Russell Casson, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1857 days.

(21) Appl. No.: 10/883,173

(22) Filed: Jun. 30, 2004

(65) Prior Publication Data

US 2006/0004335 A1    Jan. 5, 2006

(51) Int. Cl.
*A61F 13/15* (2006.01)
*A61F 13/20* (2006.01)
(52) U.S. Cl. .................................. 604/367; 604/385.01
(58) Field of Classification Search .................. 604/373, 604/367–368, 365, 358–359, 385.01; 428/447, 428/424.4, 297.4, 1.55; 442/58
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 4,340,563 A | 7/1982 | Appel et al. |
| 4,375,448 A | 3/1983 | Appel et al. |
| 4,488,928 A | 12/1984 | Ali Khan et al. |
| 4,494,278 A | 1/1985 | Kroyer et al. |
| 4,640,810 A | 2/1987 | Laursen et al. |
| 5,128,082 A | 7/1992 | Makoui |
| 5,378,528 A | 1/1995 | Makoui |
| 5,527,171 A | 6/1996 | Soerensen |
| 5,883,231 A | 3/1999 | Achter et al. |
| 5,981,689 A | 11/1999 | Mitchell et al. |
| 6,060,636 A | 5/2000 | Yahiaoui et al. |
| 6,072,101 A | 6/2000 | Beihoffer et al. |
| 6,087,448 A | 7/2000 | Mitchell et al. |

(Continued)

FOREIGN PATENT DOCUMENTS

CA    2 370 380 A1    10/2001

(Continued)

OTHER PUBLICATIONS

Neumann, A.W., and R.J. Good, "Techniques of Measuring Contact Angles," Chapter 2 of *Surface and Colloid Science*, vol. 11, Experimental Methods, edited by R.J. Good and R.R. Stromberg, Plenum Press, 1979, pp. 31-91.

*Primary Examiner* — Michele M Kidwell
(74) *Attorney, Agent, or Firm* — Denise L. Stoker; Bryan R. Rosiejka (57) ABSTRACT

A unitary absorbent core includes a nonwoven layer which has a body-facing surface and a garment-facing surface. At least a portion of a first binding agent is impregnated into the garment-facing surface. A superabsorbent material is located on the impregnated surface, and a second binding agent is located on the superabsorbent material and can be superimposed onto the first binding agent. The unitary absorbent core can be utilized for absorbing viscous fluids.

23 Claims, 5 Drawing Sheets

U.S. PATENT DOCUMENTS

| | | | |
|---|---|---|---|
| 6,121,409 | A | 9/2000 | Mitchell et al. |
| 6,159,591 | A | 12/2000 | Beihoffer et al. |
| 6,194,631 | B1 | 2/2001 | Mitchell et al. |
| 6,222,091 | B1 | 4/2001 | Beihoffer et al. |
| 6,235,965 | B1 | 5/2001 | Beihoffer et al. |
| 6,342,298 | B1 | 1/2002 | Evans et al. |
| 6,348,253 | B1 | 2/2002 | Daley et al. |
| 6,376,072 | B1 | 4/2002 | Evans et al. |
| 6,392,116 | B1 | 5/2002 | Beihoffer et al. |
| 6,403,857 | B1 | 6/2002 | Gross et al. |
| 6,509,512 | B1 | 1/2003 | Beihoffer et al. |
| 6,525,240 | B1 * | 2/2003 | Graef et al. .................. 604/383 |
| 6,555,502 | B1 | 4/2003 | Beihoffer et al. |
| 6,562,742 | B2 * | 5/2003 | Dutkiewicz et al. .......... 442/375 |
| 6,645,407 | B2 | 11/2003 | Kellenberger et al. |
| 6,664,437 | B2 * | 12/2003 | Sawyer et al. ................ 604/365 |
| 6,723,892 | B1 | 4/2004 | Daley et al. |
| 2001/0001312 | A1 | 5/2001 | Mitchell et al. |
| 2001/0007064 | A1 | 7/2001 | Mitchell et al. |
| 2001/0029358 | A1 | 10/2001 | Beihoffer et al. |
| 2001/0044612 | A1 | 11/2001 | Beihoffer et al. |
| 2002/0007166 | A1 | 1/2002 | Mitchell et al. |
| 2002/0007169 | A1 * | 1/2002 | Graef et al. .................. 604/378 |
| 2002/0013560 | A1 * | 1/2002 | Erspamer et al. ............. 604/381 |
| 2002/0015846 | A1 | 2/2002 | Evans et al. |
| 2003/0014027 | A1 | 1/2003 | Beihoffer et al. |
| 2003/0044562 | A1 | 3/2003 | Li et al. |

FOREIGN PATENT DOCUMENTS

| | | |
|---|---|---|
| EP | 1 417 946 A1 | 5/2004 |
| WO | WO 99/25393 A2 | 5/1999 |
| WO | WO 99/25745 A1 | 5/1999 |
| WO | WO 99/25748 A1 | 5/1999 |
| WO | WO 00/56959 A1 | 9/2000 |
| WO | WO 00/63295 A1 | 10/2000 |
| WO | WO 02/10032 A2 | 2/2002 |
| WO | WO 03/018671 A1 | 3/2003 |
| WO | WO 03/037392 A1 | 5/2003 |

* cited by examiner

UNITARY ABSORBENT CORE WITH BINDING AGENTS

FIELD OF THE INVENTION

The present invention relates to an absorbent article. More particularly, the present invention pertains to a unitary absorbent core for an absorbent article, such as disposable diapers and training pants, feminine hygiene products, and adult incontinence products.

BACKGROUND OF THE INVENTION

Absorbent materials and absorbent articles have a wide variety of uses. Examples include personal care products, such as disposable diapers and training pants; feminine hygiene products, such as sanitary napkins and tampons; adult incontinent care products, such as pads and undergarments; and health care items such as bandages and wound dressings. Other absorbent materials and absorbent articles include wipers, absorbent mats and soakers.

Viscous fluids are often difficult to absorb into such absorbent products. Such fluids include menses, runny feces (or bowel movements), exudates from wounds, mucus, and fluids containing food and plant proteins. For example, menses is a viscoelastic fluid composed of blood (primarily red blood cells and plasma), cervical mucus and/or tissue fragments. In feminine hygiene products, the viscoelastic properties of menses often make it challenging to absorb and distribute within the products. The viscosity and/or elastic components of such fluids tend to impose certain requirements for absorption and/or distribution within the absorbent core component of an absorbent article which can be inconsistent with the requirements typical of fluids that are less viscous or elastic, often resulting in a compromise in overall performance. For instance, the pore and capillary sizes in an ideal material for absorbing and distributing less viscoelastic components may be different from those that work best for the more viscoelastic components.

Viscous fluids may cause other challenges as well. For example, because of the viscosity and/or composition, the intake of such fluids through the surface of an absorbent core can be impeded. Likewise, fluid distribution, retention capacity, and rewet performance can be reduced as well. Therefore, when additional insults of viscous fluids come into contact with a surface of an absorbent core, the additional insults often cause the absorbent product to leak.

To compensate for such disadvantages, absorbent cores designed for absorbing viscous fluids, such as menses, tend to comprise multiple layers. For example, such absorbent cores have included various systems of liquid-handling layers, such as intake layers, distribution layers, retention layers, and the like. As each layer is added, the physical thickness of the liquid-handling system increases, while production efficiencies generally decrease and production costs generally increase. As a result, there is a continued desire for a liquid-handling system which absorbs a broad range of fluid types, is increasingly thinner, is more efficient to manufacture, and is less costly to produce.

SUMMARY

In response to the discussed disadvantages and needs, a new absorbent core has been discovered. Generally stated, the present invention provides an absorbent core that is unitary in structure yet can intake, distribute and retain viscous fluids, such as menses, in a similar fashion to multi-layer absorbent cores.

The unitary absorbent core of the present invention comprises a single nonwoven layer. The nonwoven layer has a body-facing surface and an opposing garment-facing surface. A first binding agent is at least partially impregnated into the garment-facing surface of the nonwoven layer. Superabsorbent materials are located on the impregnated garment-facing surface of the nonwoven layer. A second binding agent is located on the superabsorbent material and can be superimposed onto the first binding agent. The second binding agent can, among other things, secure attachment of the superabsorbent materials to the impregnated garment facing surface. In one example, the invention may further comprise additional additives, such as an odor reducing agent or a fluid modifying agent.

The nonwoven layer may comprise structures known to those skilled in the art. In one example, the nonwoven layer is an airlaid. In another example, the nonwoven layer can be a bonded carded web. In other examples, the nonwoven layer can have various absorbent capacities, densities, basis weights, and/or sizes which are selectively configured to provide desired combinations of viscous fluid intake rate, absorbent retention capacity, rewet performance, horizontal wicking, desorption, shape maintenance, and aesthetics.

The first binding agent is impregnated into the surface of the nonwoven layer that is opposite the body-facing surface or the source of insult (hereinafter the "garment-facing surface"). In general, the first binding agent should not restrict the absorbency properties of the superabsorbent material. When applied, the first binding agent creates an interface within the nonwoven layer, and increases the density of the garment-facing portion of the nonwoven. This may have resulted in improved wicking of the viscous fluid in the x, y, and z directions in the structure, as seen in the Examples below. Furthermore, a greater quantity of viscous fluid is drawn from the body-facing surface of the nonwoven layer to the surface containing the binding agent and superabsorbent material, when compared to a nonwoven layer that is not impregnated with a binding agent prior to applying superabsorbent material, and/or when compared to a nonwoven layer which utilizes a binding agent that generally inhibits absorbency properties of the superabsorbent material. As a further result, a fluid stain on the body-facing surface of the unitary absorbent core can be smaller than the stain on the garment-facing surface containing the binding agent and superabsorbent material. In one example, the first binding agent is ethylene vinyl acetate latex.

Superabsorbent material is applied to the garment-facing surface of the nonwoven layer that has been impregnated with the first binding agent so that it is adjacent to, and in contact with, the surface. However, the nonwoven layer itself can remain substantially void of the superabsorbent material within its structure. One of the functions of the superabsorbent material is to collect and retain the majority of the viscous fluid insult and to draw the fluid away from the skin of the wearer. Superabsorbent materials suitable for use in the present invention are known to those skilled in the art, and may be in any operative form, such as particles, fibers, particles coated with fibers or other additives, or films.

A second binding agent is applied to the superabsorbent material can be superimposed onto the first binding agent. The second binding agent can, among other things, help secure attachment of the superabsorbent material to the garment-facing surface. This second binding agent may or may not be the same as the first binding agent. In one example, the second binding agent is ethylene vinyl acetate latex.

The manufacturing process for making the unitary absorbent core can be a continuous process or a discontinuous process, such as a batch process. Regardless of the process, the steps of applying the superabsorbent material and applying the second binding agent may alternately be repeated until a desired overall basis weight or configuration of the unitary absorbent core is obtained. The absorbent core can then be further utilized as a component of a viscous fluid absorbent article, such as an absorbent feminine care pantiliner, pad or napkin.

By incorporating its various features, the unitary absorbent core of the present invention can provide greater functionality for absorbing and wicking viscous fluids, more absorbent capacity from the same overall core shape, a thinner stature, and greater comfort and fit when compared to a multi-layer absorbent core. The unitary absorbent core of the present invention can also provide a drier feel and a cleaner and smaller stain on the body-facing surface when compared to a similar core that does not have a suitable binding agent impregnated into the garment-facing surface. Additionally, the unitary absorbent core can provide improved aesthetics and visual cues or perceptions of absorbency, and can provide greater protection and confidence to the wearer.

BRIEF DESCRIPTION OF THE DRAWINGS

These and other features, aspects, and advantages of the present invention will become better understood with regard to the following description, appended claims, and accompanying drawings.

DEFINITIONS

When introducing elements of the present invention or the preferred embodiment(s) thereof, the articles "a," "an," "the" and "said" are intended to mean that there are one or more of the elements. When employed in the present disclosure, the terms "comprises," "comprising," "including" and "having," and other derivatives from the root terms "comprise," "include" and "have" are intended to be open-ended terms that specify the presence of any stated features, elements, integers, steps, or components, and are not intended to preclude the presence or addition of one or more other features, elements, integers, steps, components, or groups thereof.

As used herein, the phrase "absorbent article" refers to devices which absorb and contain liquids. "Personal care absorbent article," "personal care product" and "feminine care article" refer to absorbent articles or devices which are placed against or near the skin to absorb and contain the various liquids discharged from the body. Examples of absorbent articles include, but are not limited to, diapers, training pants, absorbent underpants, adult incontinence products, sanitary wipes and feminine hygiene products such as pantiliners, sanitary napkins and tampons.

As used herein, the phrase "absorbent core" refers to the component of an absorbent article that intakes and retains a majority of a fluid insult.

As used herein, the term "airlaid" is well defined in literature and documented in the art. Examples include the Dan-Web process as described in U.S. Pat. No. 4,640,810 Laursen et al. assigned to Scan Web of North America Inc; the Kroyer process as described in U.S. Pat. No. 4,494,278 Kroyer et al. and U.S. Pat. No. 5,527,171 Soerensen assigned to Niro Separation a/s; the method of U.S. Pat. No. 4,375,448 Appel et al. assigned to Kimberly-Clark Corporation, or other similar methods. The webs produced by these methods are subsequently bonded together to form an adequate tensile strength web by thermal fusing, latex bonding or combinations thereof, which are well known in the art.

As used herein, the phrase "binding agent" refers to materials which are capable of attaching themselves to a substrate or are capable of attaching other substances to a substrate.

As used herein, the phrase "bonded carded web" refers to nonwoven webs formed by carding processes as are known to those skilled in the art and further described, for example, in coassigned U.S. Pat. No. 4,488,928 to Alikhan and Schmidt which is incorporated herein in its entirety by reference in a manner consistent with the present disclosure. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven layer.

As used herein, the phrase "fluid modifying agent" refers to an additive that can modify the flow properties of fluids, such as menses or mucin, by lysing red blood cells present in such fluids, for example. A non-limiting example includes modifying agents described in U.S. Pat. No. 6,060,636 to Yahiaoui et al. entitled "Treatment of Materials to Improve Handling of Viscoelastic Fluids," herein incorporated by reference in a manner consistent with the present disclosure.

As used herein, the term "foamable" refers to a material that is a partly or substantially stable foam that can be produced by mechanical agitation in the presence of air or upon application of other foaming methods mentioned herein and known to those skilled in the art. Pure water is not foamable, for example, whereas egg whites and many aqueous surfactant solutions are.

As used herein, the term "hydrophobic" refers to a material having a contact angle of water in air of at least 90 degrees. In contrast, as used herein, the term "hydrophilic" refers to a material having a contact angle of water in air of less than 90 degrees. For the purposes of this application, contact angle measurements are determined as set forth in Robert J. Good and Robert J. Stromberg, Ed., in "Surface and Colloid Science—Experimental Methods," Vol. II, (Plenum Press, 1979), herein incorporated by reference in a manner consistent with the present disclosure.

As used herein, the term "intake" refers to the ability of an absorbent article to absorb fluid. Intake time is used to assess the quality of absorption with lower intake times denoting materials capable of rapid absorption and higher intake times denoting materials with poorer absorption.

As used herein, the term "interface" refers to the surface within the nonwoven layer which divides the binding agent impregnated portion from the binding agent-free portion.

As used herein, the term "menses simulant" is a material that simulates the viscoelastic and other properties of menses. The phrase "menses simulant" describes a liquid generally characterized as being a viscoelastic fluid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water, and the like, are generally characterized as having a relatively low viscosity and comprising one or more components having homogeneous physical and/or chemical properties. As a result of having homogeneous properties, the one or more components of simple liquids behave substantially similarly during absorption or adsorption, although some components may be absorbed or adsorbed more readily than others. Although a complex liquid is generally characterized herein as including specific components having inhomogeneous properties, each specific component of a complex liquid generally has homogeneous properties. Consider for example a representative complex body-liquid having three specific components: red blood cells, blood protein molecules, and water molecules. Upon examination, one skilled in the art could easily distinguish between each of the three specific components according to their generally inhomogeneous properties. Moreover, when examining a particular specific component, such as the red blood cell component, one skilled in the art could easily recognize the generally homogeneous properties of the red blood cells. Two menses simulants are used for testing of this invention. Menses simulant A is composed of swine blood diluted with swine plasma to provide a hematocrit level of 35-percent (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed. Simulant A is typically used for absorbent capacity tests. Menses simulant B is swine blood diluted to a hematocrit level of 30-percent by volume, with sheared, thick egg white added to mimic the mucin component of menses. This simulant is available from Cocalico Biologicals, Inc., a business having offices located in Reamstown, Pa., U.S.A.; and is also described in U.S. Pat. No. 5,883,231 entitled MENSES SIMULANT by A. Achter et al. granted Mar. 16, 1999, the entire disclosure of which is incorporated herein in a manner that is consistent herewith.

As used herein "multi-layer absorbent core" means an absorbent laminate having two or more nonwoven layers.

As used herein, the term "nonwoven layer" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes, such as for example, meltblowing processes, spunbonding processes, airlaying processes, coforming processes and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the phrase "open nonwoven" refers to a nonwoven layer having a density of about 0.12 g/cc or less.

The terms "particle," "particles," "particulate," "particulates" and the like, mean that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "polymer" generally includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "spunbond" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al., herein incorporated by reference in a manner consistent with the present disclosure. Spunbond fibers are quenched and generally not tacky when they are deposited onto a collecting surface. Spunbond fibers are generally continuous and have average diameters frequently larger than 7 microns, more particularly, between about 10 and 20 microns.

As used herein, the term "stain" refers to fluid, wet or dried, which is present on the top surface, in, or on the bottom surface of a nonwoven layer or unitary absorbent core of the present invention. A "stain" is generally visible to the user of the absorbent article.

As used herein, the term "superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. The superabsorbent material may be biodegradable or non-biodegradable. The superabsorbent materials can include particles, fibers, tows, flakes, particles coated with fibers or other additives, films, foams, and the like. A material is "absorbent" if it absorbs at least five times its weight of the aqueous solution under these conditions.

As used herein, the term "surfactant" includes a single surfactant or a mixture of two or more surfactants. If a mixture of two or more surfactants is employed, the surfactants may be selected from the same or different classes, provided only that the surfactants present in the mixture are compatible with each other. In general, the surfactant can be any surfactant known to those having ordinary skill in the art, including anionic, cationic, and nonionic surfactants. Examples of anionic surfactants include, among others, linear and branched-chain sodium alkylbenzenesulfonates, linear and branched-chain alkyl sulfates, and linear and branched-chain alkyl ethoxy sulfates. Cationic surfactants include, by way of illustration, tallow trimethylammonium chloride. Examples of nonionic surfactants, include, again by way of illustration only, alkyl polyethoxylates; polyethoxylated alkylphenols; fatty acid ethanol amides; and complex polymers of ethylene oxide, propylene oxide, and alcohols.

The phrase "the two-layer core" refers to the current commercially available two-layer core found in KOTEX ULTRATHIN MAXI sanitary pads, available from Kimberly-Clark Corporation, a business having offices located in Neenah, Wis., U.S.A. The two-layer core has a first (top) airlaid material layer comprising 90-percent semi-treated woodpulp fluff and 10-percent bicomponent binder fiber, and has a basis weight of about 175 gsm and a density of about 0.06 g/cc. The two-layer core further has a second (bottom) airlaid layer comprising 76.5-percent untreated woodpulp fluff fiber, 8.5-percent bicomponent binder fiber, and 15-percent SXM 9394 superabsorbent material available from Stockhausen Inc., a business having offices located in Greensboro, N.C., U.S.A., and has a basis weight of 225 gsm and a density of about 0.12 g/cc.

The phrase "TGI Ratio" refers to the triple gush intake time for any of the first, second, or third insults of a unitary absorbent core sample divided by the triple gush intake time for the corresponding first, second, or third insult of the two-layer core (defined above), as measured by the Triple Gush Intake Test described in the Examples below.

The phrase "unitary absorbent core" refers to an absorbent core comprising only one nonwoven layer or laminate.

As used herein, the term "viscoelastic" means a composition having at least one significant component that is moderately viscous and/or has elastic properties. By "moderately viscous" it is meant that the component has a viscosity of at least that of normal human blood plasma. By "elastic" it is meant that the component has elasticity equal to or greater than normal human blood.

As used herein, the phrase "viscous fluid" refers to a fluid having a viscosity greater than the viscosity of water, including such fluids as menses, menses simulant, runny feces (or bowel movements), exudates from wounds, mucus, fluids containing food and plant proteins, and the like.

The preceding terms and phrases may be defined with additional language in the remaining portions of the specification.

DETAILED DESCRIPTION

The present invention relates to an absorbent article. More particularly, the present invention pertains to a unitary absorbent core as a component for an absorbent article, such as an absorbent feminine care pantiliner or sanitary napkin.

Figure 1:
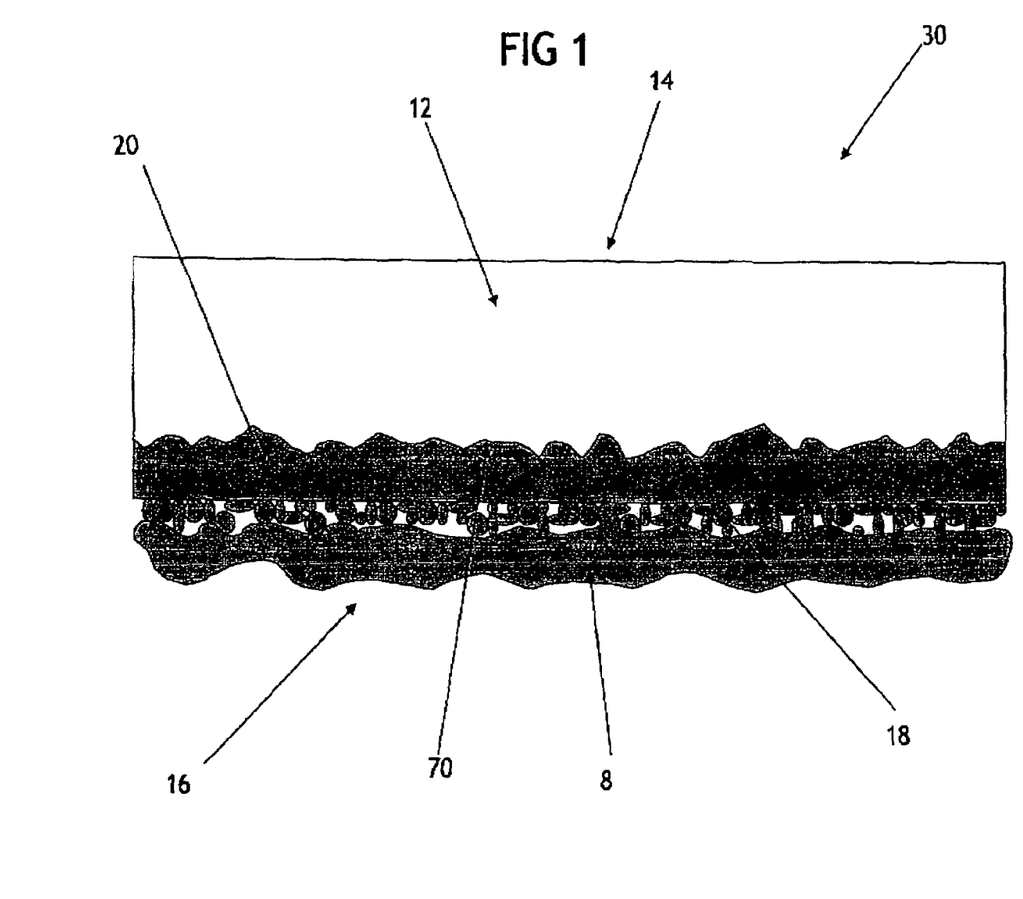
FIG. 1 shows a cross-section of a representative unitary absorbent core.

Referring to FIG. 1, the unitary absorbent core 30 of the present invention comprises a single nonwoven layer 12 having a body-facing surface 14 and a garment-facing surface 16. The absorbent core further comprises a first binding agent 20 at least partially impregnated into the garment-facing surface 16 of the nonwoven layer 12. The garment-facing surface 16 will typically oppose the body-facing surface 14. The unitary absorbent core further comprises a superabsorbent material 18 located adjacent to and/or in contact with the first binding agent 20, such that the nonwoven layer 12 can remain substantially void of superabsorbent material. At least a portion of the first binding agent may be present between the superabsorbent material and the garment-facing surface. A second binding agent 8, which may be the same as the first binding agent 20, is applied to the superabsorbent material 18, and can be superimposed (not shown) onto the first binding agent 20. Optionally, other additives (not shown) may be added to the invention, such as an odor reducing agent or a fluid modifying agent. For example, suitable fluid modifying agents are described in U.S. Pat. No. 6,060,636 to Yahiaoui et al. entitled "Treatment of Materials to Improve Handling of Viscoelastic Fluids," which is herein incorporated by reference in a manner consistent with the present disclosure.

In general, the nonwoven layer may include natural fibers, synthetic fibers, foams, scrims, wet-laid fibrous webs, airlaid webs, spunbond webs, meltblown fabric, carded webs, bonded carded webs, bicomponent spunbond webs, coform webs, film/nonwoven laminates, apertured films or the like, as well as combinations thereof. Other examples of suitable materials for constructing the nonwoven layer include rayon, bonded carded webs of polyester, polypropylene, polyethylene, nylon, or other heat-bondable fibers, polyolefins such as copolymers of polypropylene and polyethylene, linear low-density polyethylene, aliphatic esters such as polylactic acid, finely perforated film webs, net materials, and the like, as well as combinations thereof. The nonwoven may be stretchable, elastic, or extensible. The unitary absorbent core 30 of the present invention utilizes materials that are configured to quickly absorb and pull viscous fluids away from the body-facing surface 14 and to distribute and store such fluids in a manner that is consistent with desirable rewet performance. Accordingly, the unitary absorbent core 30 can provide at least the functions of fluid intake, fluid distribution, fluid spreading, temporary storage, fluid retention and rewet performance.

The unitary absorbent core 30 of the present invention is suitably constructed from an open structure with high intake for viscous fluids, such as a nonwoven material having a density less than 0.12 g/cc. One example of the present invention utilizes a nonwoven airlaid. One such airlaid is comprised of 90-percent NF 405 available from Weyerhaeuser Company, a business having offices located in Federal Way, Wash., U.S.A. and 10-percent bicomponent binder fiber T-255 available from KoSa, a business having offices located in Houston, Tex., U.S.A., and has a basis weight of about 200 gsm and a density of about 0.06 g/cc.

Various physical properties of the nonwoven layer 12, such as density and basis weight, may be manipulated to obtain a desired intake for viscous fluids. For example, a high intake may be achieved by utilizing a nonwoven material having a low density. One suitable material has a density in the range of about 0.02 g/cc to about 0.12 g/cc, such as about 0.02 g/cc to about 0.08 g/cc. In another example, the material suitably has a basis weight in the range of about 30 gsm to about 300 gsm. In one particular example of the present invention, the unitary absorbent core 30 comprises an airlaid material having a basis weight of about 175 gsm at a density of about 0.06 g/cc. In another particular example, the unitary absorbent core 30 comprises an airlaid material having a basis weight of 200 gsm at a density of 0.06 g/cc. It is contemplated that other combinations within the specified ranges of basis weight and density may also be utilized without departing from the scope of the invention.

When the unitary absorbent core 30 is used as a component of an absorbent article, various disadvantages may occur if the basis weight or the density of the nonwoven layer is outside the desired range. For example, a basis weight that is higher than the desired range can provide for an absorbent article that is excessively bulky or generally uncomfortable to the wearer during use. Additionally, the product cost may become higher than desired. Alternatively, a basis weight that is lower than the desired range can excessively increase the incidence of bunching, twisting and roping of an absorbent article, and may negatively impact the overall integrity of the absorbent core or absorbent article. In either case, the overall efficacy and perception of performance of the unitary absorbent core 30 may be reduced, and consumer confidence in the product may decline.

Likewise, when used as a component of an absorbent article, various disadvantages may occur if the density of the nonwoven layer 12 is outside the desired range. For example, density that is higher than the desired range can provide an excessively stiff article which is uncomfortable during use. Furthermore, an overly high density can excessively reduce the permeability and absorbent capacity of the unitary absorbent core. As a result, viscous liquid intake and transfer can be less than desired and the absorbent article can prematurely leak. Alternatively, a density that is lower than the desired range can provide a product that is too thick, ill fitting, and uncomfortable. Also, the permeability can become too high, and the unitary absorbent core may be unable to adequately remove fluid from a layer above the absorbent core, such as a topsheet, in an absorbent article. As a result, there can be excessive rewet and flowback of liquid to the wearer's skin. In either case, the overall efficacy of the unitary absorbent core 30 may be reduced, and consumer confidence in the product may decline.

The unitary absorbent core 30 includes a first binding agent 20 which is at least partially impregnated into the garment-facing surface 16 of the nonwoven layer 12. The first binding agent 20 provides several functions, among which is forming an interface 70 within the nonwoven layer 12 to help promote wicking of a viscous fluid insult in the x, y, and z directions. Another purpose of the first binding agent 20 can be to provide adhesion of the superabsorbent material 18, as well as any additional additives which may optionally be applied, to the garment-facing surface 16 of the nonwoven layer 12.

The first binding agent 20 can be a polymeric material. It may be rendered foamable at least in part due to the presence of foaming agents such as a surfactant, including anionic, nonionic, and cationic surfactants, which may be present in the nonwoven layer. It may also be rendered more wettable, at least in part, due to the presence of a surfactant. In one example, a surfactant under the trade name AEROSOL OT, available from Cytec Industries, Inc., a business having offices located in West Patterson, N.J., U.S.A., was added to the first binding agent 20 to improve wettability properties. The first binding agent 20 can also contain a plasticizer to make the dried binding agent soft and flexible for comfort during use in an absorbent article.

The first binding agent 20 material may or may not be water swellable and water insoluble. In general, the binding agent material for absorbent articles is substantially water insoluble, even when the binding agent material is water swellable. In the Examples, the first binding agent 20 material may provide not only good dry stability but also good wet stability and wet resiliency to the unitary absorbent core 30 when wetted by a viscous fluid insult. In the Examples, a suitable first binding agent 20 resulted in a unitary absorbent core which exhibited a TGI Ratio of 1.2 or less, as defined above.

First binding agents 20 which are also suitable for use in the Examples of the present invention include binding agents which are finely dispersed emulsions. Suitably, the first binding agent is a latex-based emulsion with a solids content of about 2-percent to about 60-percent. A first binding agent 20 in emulsion form can be further diluted with water to desired viscosities for applying to the nonwoven layer. For example, if spraying is selected as the method for application, a solids content of between about 2-percent to about 25-percent would be suitable.

The first binding agent 20 can be applied to the garment-facing surface 16 of the nonwoven layer 12 at a level such that the total amount of all binding agents is in the range of about 5 gsm to about 80 gsm, such as from about 10 gsm to about 60 gsm. In one example, the total binding agent add-on level was about 30 gsm. In another example, the total binding agent add-on level was about 45 gsm. In still another example, the total binding agent add-on level was about 60 gsm.

The first binding agent 20 can be applied to the nonwoven layer 12 using any number of methods known in the art. These methods include, but are not limited to, spraying, foaming, brushing, printing, and the like. In one example, the first binding agent 20 can be sprayed onto a surface of the nonwoven layer 12 in a continuous manufacturing process. The depth of impregnation of the first binding agent 20 into the nonwoven layer 12 is controlled by such factors as binding agent add-on level, viscosity of the binding agent formulation, speed of application, speed of the moving nonwoven layer, and the like. Additionally, the first binding agent 20 can be allowed to at least partially dry prior to the addition of the superabsorbent material 18.

It is contemplated that any binding agent may be used, but it is suitable that it does not restrict absorbency properties of the superabsorbent material 18 in such a way that results in slow intake, low capacity, poor wicking performance, poor rewet performance, and/or poor desorption performance during insults of viscous liquids. One suitable measure for purposes of the invention is that the resulting absorbent core exhibits a TGI Ratio of 1.2 or less, as defined above.

In one example, the first binding agent 20 was ethylene vinyl acetate (EVA) latex. A suitable EVA latex binding agent is AIRFLEX 192, available from Air Products and Chemicals, Inc., a business having offices located in Allentown, Pa., U.S.A. Another suitable EVA latex binding agent is DUR-O-SET ELITE ULTRA 25-135A, available from National Starch and Chemical Company, a business having offices located in Bridgewater, N.J., U.S.A. Still another suitable EVA latex binding agent is DUR-O-SET ELITE 33, also available from National Starch and Chemical Company.

First binding agents which result in a unitary absorbent core that exhibits a TGI Ratio greater than 1.2 are considered as non-working binding agents for purposes of the invention. One such non-working binding agent is a latex binding agent with the trade name RHOPLEX B-15R, available from Rohm and Haas Company, a business having offices located in Philadelphia, Pa., U.S.A. For example, a sample comprising RHOPLEX B-15R (described in Table I below) resulted in a unitary absorbent core that exhibited a TGI Ratio for at least the first insult of 1.5. Furthermore, it was observed that the horizontal wicking performance of the RHOPLEX example did not exhibit an improvement when compared to the two-layer core, as seen in Table III below.

The unitary absorbent core of the present invention comprises superabsorbent material 18 located on the first binding agent impregnated garment-side surface 16 of the nonwoven layer 12. The types of superabsorbent materials suitable for use in the present invention are known to those skilled in the art, and may be in any operative shape, form and size, such as particulates, fibers, particles coated with fibers or other additives, or films, for example. Generally stated, the superabsorbent material 18 can be a hydrogel-forming polymeric absorbent material which may be formed from organic hydrogel-forming polymeric material, and may include natural material such as agar, pectin, and guar gum; modified natural materials such as carboxymethyl cellulose and other biodegradable superabsorbent materials, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, polyalkylene oxide, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and hydrolyzed isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors. One suitable superabsorbent material for the present invention is SXM 9394, available from Stockhausen Inc., a business having offices located in Greensboro, N.C., U.S.A.

Other superabsorbent materials include multicomponent superabsorbent particulate gels. One such material is BASF E1231-99, available from BASF, a business having offices located in Ludwigshafen, Germany. Multicomponent superabsorbent gel particles and methods to prepare them are described in U.S. Pat. Nos. 5,981,689; 6,072,101; 6,087,448; 6,121,409; 6,159,591; 6,194,631; 6,222,091; 6,235,965; 6,342,298; 6,376,072; 6,392,116; 6,509,512; and 6,555,502; U.S. Patent Publications 2001/01312; 2001/07064; 2001/29358; 2001/44612; 2002/07166; 2002/15846; and 2003/14027; and PCT Publications WO 99/25393; WO 99/25745; WO 99/25748; WO 00/56959; WO 00/63295; WO 02/10032; WO 03/18671; and WO 03/37392; the disclosures of which are herein incorporated by reference in a manner consistent with the present disclosure.

In general, a desired basis weight of superabsorbent material 18 is applied to the garment-facing surface of the nonwoven layer 12 in which the first binding agent 20 was previously impregnated. The superabsorbent material 18 can be added at a level in the range of about 5 gsm to about 150 gsm, such as from about 30 gsm to about 90 gsm. In one example, the superabsorbent add-on level was about 30 gsm. In another example, the superabsorbent add-on level was about 45 gsm. In another example, the superabsorbent add-on level was about 60 gsm. In still another example, the superabsorbent add-on level was about 90 gsm.

There are numerous methods for applying superabsorbent material 18 to the impregnated garment-facing surface 16 of the nonwoven layer 12. Exemplary means include sprinkling, printing, spraying, painting, and other similar methods known to those skilled in the art. The superabsorbent materials may also be formed directly on the nonwoven layer 12 by in-situ polymerization, such as that taught in U.S. Pat. No. 6,645,407 to Kellenberger et al. entitled "Process for Making Absorbent Material with In-Situ Polymerized Superabsorbent" herein incorporated by reference in a manner consistent with the present disclosure. Application processes for superabsorbent material 18 may be continuous or discontinuous, and can additionally include cascading, waterfall spread-feeding, and vibration feeding. Suitably, the superabsorbent materials are placed uniformly onto the impregnated garment-facing surface 16 of the nonwoven layer 12.

The unitary absorbent core 30 of the present invention also includes a second binding agent 8 which is applied to the superabsorbent material 18 and can be superimposed (not shown) onto the first binding agent 20. One of the purposes of the second binding agent 8 is to help secure attachment of the superabsorbent material 18 to the impregnated garment-facing surface 16 of the nonwoven layer 12. The second binding agent 8 can also provide an attachment means for any additional additives (not shown) which may optionally be applied.

The second binding agent 8 can be a polymeric material. It may be rendered foamable at least in part due to the presence of foaming agents such as a surfactant, including anionic, nonionic, and cationic surfactants, which may be present in the nonwoven layer. It may also be rendered more wettable, at least in part, due the presence of a surfactant. In one example, a surfactant under the trade name AEROSOL OT, available from Cytec Industries, Inc., a business having offices located in West Patterson, N.J., U.S.A., was added to the second binding agent 8 to improve wettability properties. The second binding agent 8 can also contain a plasticizer to make the dried binding agent soft and flexible for comfort during use in an absorbent article.

Suitable second binding agents 8 include, but are not limited to, finely dispersed emulsions. For example, the second binding agent 8 can be a latex-based emulsion with a solids content of about 2-percent to about 60-percent. A second binding agent 8 in emulsion form can be further diluted with water to desired viscosities for applying to the superabsorbent material 18. For example, if spraying is selected as the method for application, a solids content of between about 2-percent to about 25-percent would be suitable.

The second binding agent 8 can be applied to the superabsorbent material 18 and can be superimposed onto the first binding agent 20 such that the total amount of all binding agents in the unitary absorbent core 30 is in the range of about 5 gsm to about 80 gsm, such as from about 10 gsm to about 60 gsm. In one example, the total binding agent add-on level was about 30 gsm. In another example, the total binding agent add-on level was about 45 gsm. In still another example, the total binding agent add-on level was about 60 gsm. Alternatively, the amount of first binding agent 20 in the combined total amount of first and second binding agent can range from about 10-percent to about 70-percent by weight, such as about 25-percent to about 50-percent by weight.

The second binding agent 8 can be applied to the nonwoven layer 12 using any number of methods known in the art. These methods include, but are not limited to, spraying, foaming, brushing, printing, and the like. In one example, the second binding agent 8 is sprayed onto the superabsorbent material 18 in a continuous manufacturing process. The add-on level of second binding agent 8 can be controlled by such factors as viscosity of the binding agent formulation, speed of application, speed of the moving nonwoven layer, and the like.

It is contemplated that any second binding agent 8 may be used, but it is suitable that it does not adversely affect absorbency properties of the superabsorbent material 18 in such a way that results in slow intake, low capacity, poor wicking performance, poor rewet performance, and/or poor desorption performance during insults of viscous liquids. One such measure is that the selection of the binding agent(s) results in a unitary absorbent core which exhibits a TGI Ratio of 1.2 or less, as defined above.

In one example, the second binding agent 8 was ethylene vinyl acetate (EVA) latex. One suitable EVA latex binding agent is AIRFLEX 192, available from Air Products and Chemicals, Inc., a business having offices located in Allentown, Pa., U.S.A. Another suitable EVA latex binding agent is DUR-O-SET ELITE ULTRA 25-135A, available from National Starch and Chemical Company, a business having offices located in Bridgewater, N.J., U.S.A. Still another suitable EVA latex binding agent is DUR-O-SET ELITE 33, also available from National Starch and Chemical Company.

Figure 2:
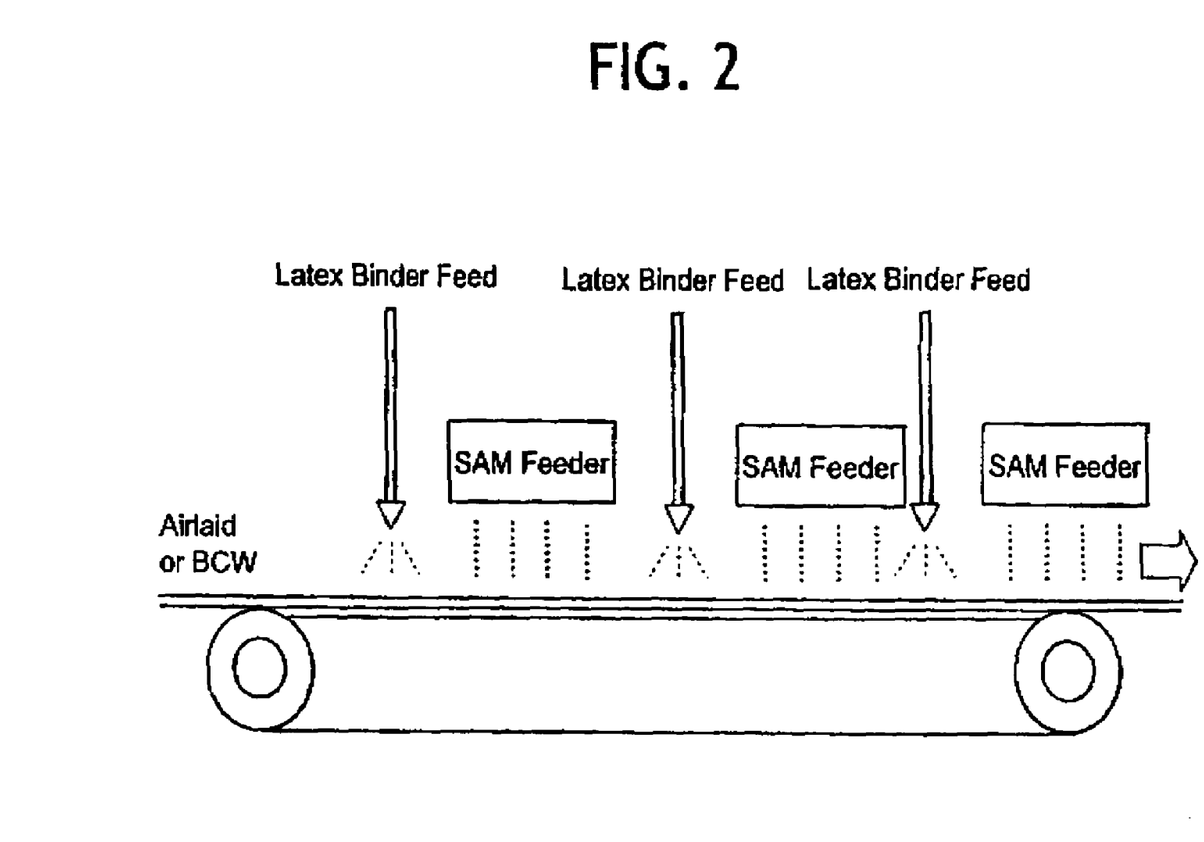
FIG. 2 shows a schematic of a continuous process for the invention.

The manufacturing process for making the unitary absorbent core 30 can be a continuous process or a discontinuous process, such as a batch process. For example, with reference to FIG. 2, in a continuous airlaid or bonded carded web process, a nonwoven layer is formed using conventional methods known in the art. Following formation of the nonwoven layer, a desired basis weight of a first binding agent is sprayed onto, and at least partially impregnates into, a surface of the non-woven layer. A desired amount of superabsorbent material is then applied by use of a commercial air forming process, for example, to the impregnated surface. Optionally, some form of pressure, such as mechanical or air pressure, may be applied onto the superabsorbent material at this time to secure the superabsorbent material onto the nonwoven layer. A desired basis weight of second binding agent is then subsequently sprayed onto the superabsorbent material and can be superimposed onto the first binding agent. Optionally, there may be alternating subsequent additions of superabsorbent material and second binding agent, as well as additions of other functional additives (not shown), such as an odor reducing agent or a fluid modifying agent. The subsequent applications of superabsorbent material and binding agent can be repeated until a desired total add-on level is reached for both constituents. For example, it may be desired that the total add-on level of binding agent does not exceed an amount in the range of about 5 gsm to about 80 gsm, and that the total add-on level of superabsorbent material does not exceed an amount in the range of about 5 gsm to about 150 gsm. It is also contemplated that subsequent applications of superabsorbent materials and/or binding agents may or may not be the same materials as in previous applications.

As discussed above, the first binding agent 20, the superabsorbent material 18, and the second binding agent 8 are applied to the garment-facing surface 16 of the nonwoven layer 12. This configuration provides a better ability to 'lock in' and hold the absorbed viscous fluid, while keeping the majority of the fluid away from the wearer's skin. This, in turn, improves protection and increases confidence of the wearer.

It was discovered that the unitary absorbent core 30 of the present invention also exhibits improved wicking capability for viscous fluid insults when compared to the two-layer core (defined above).

Figure 3:
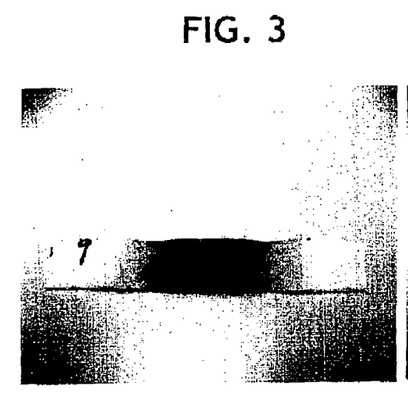
FIG. 3 shows a top view stain area of a representative unitary absorbent core.
Figure 4:
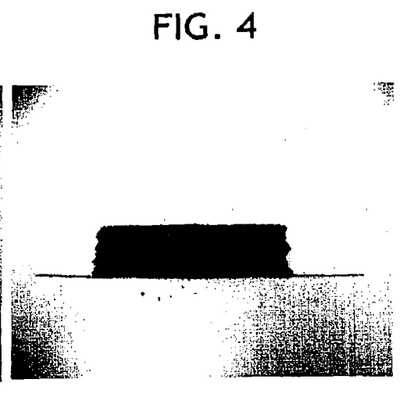
FIG. 4 shows a bottom view stain area of a representative unitary absorbent core.
Figure 5:
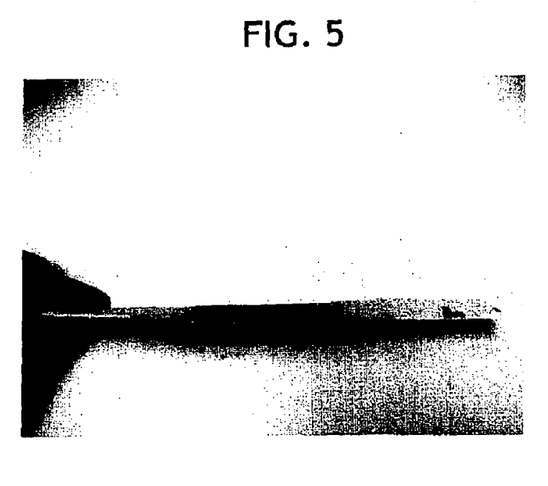
FIG. 5 shows a cross-section view stain area of a representative unitary absorbent core.

Images of an exemplary unitary absorbent core 30 of the present invention are shown in FIGS. 3, 4 and 5. FIG. 3 shows a topview (i.e., view of the body-facing surface) of the unitary absorbent core 30, providing a menses simulant stain area of light density, indicating a lower concentration of red blood cells, and a relatively limited wicking distance in the longitudinal direction. FIG. 4 shows a bottom view (i.e., view of the garment-facing surface containing the binding agents and superabsorbent material) of the absorbent core, providing a menses simulant stain area which is significantly darker, indicating a higher concentration of red blood cells, and at least double the wicking distance in the longitudinal direction when compared to the top side. FIG. 5 shows a cross-section of the absorbent core which exemplifies the wicking characteristics from the top to the bottom of the unitary absorbent core 30. The top side or body-facing surface of the core has a shorter wicking distance, while the bottom side or garment-facing surface has a significantly longer wicking distance. Thus, the unitary absorbent core 30 of the present invention has the ability to bottom load the menses simulant.

Figure 6:
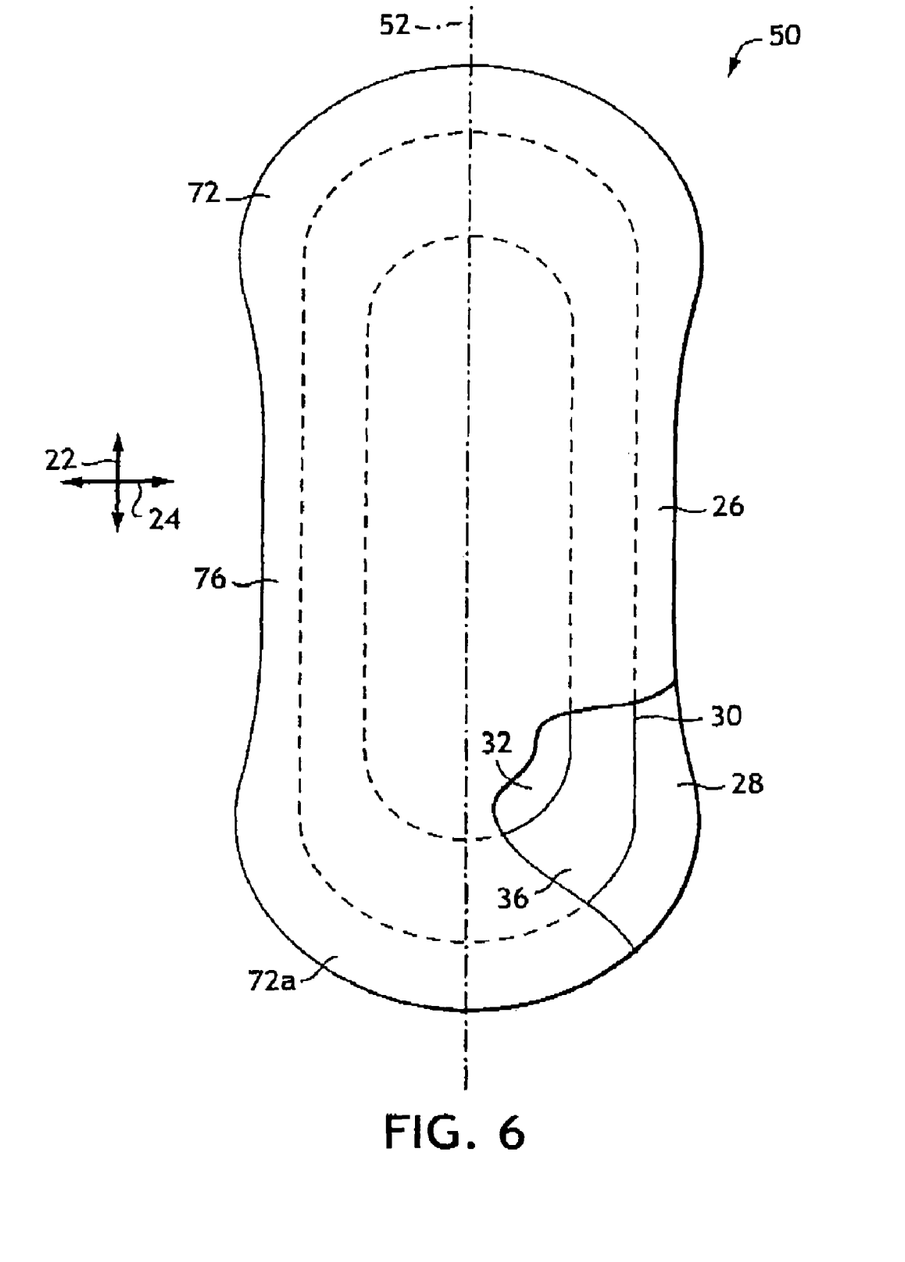
FIG. 6 shows a representative, partially cut-away, top view of a garment-side of an absorbent article which includes the unitary absorbent core as a component.

The unitary absorbent core 30 of the present invention may be utilized as a component of an absorbent article. For example, the absorbent article may be a feminine care article, such as an absorbent feminine care pantiliner, pad or napkin. FIG. 6 illustrates an example of a suitable article, such as the representatively shown feminine care article 50, which is configured to incorporate the present invention. The feminine care article can have a lengthwise longitudinal direction 22, a transverse, laterally extending, cross-direction 24, first and second longitudinally opposed end portions 72 and 72a, and an intermediate portion 76 located between the end portions. As representatively shown, the longitudinal dimension of the article is relatively larger than the lateral dimension of the article. The article 50 can include a top sheet or cover 26, a baffle 28, and the unitary absorbent core 30 of the present invention positioned between the cover and baffle. The unitary absorbent core 30 can have configurations of absorbent capacities, densities, basis weights and/or sizes which are selectively constructed and arranged to provide desired combinations of liquid intake time, absorbent saturation capacity, absorbent retention capacity, z-directional liquid distribution along the thickness dimension of the article, horizontal wicking, rewet performance, desorption performance, shape maintenance, and aesthetics.

By incorporating its various features, aspects and configurations, alone or in desired combinations, the article can provide an improved absorbent system that can take better advantage of the functional properties of the unitary absorbent core of the present invention. For example, the article can provide comparable or improved absorbent capacity when compared to an article comprising a multi-layered absorbent core, such as the two-layer core. Similarly, the article can provide comparable or improved absorbent capacity while reducing the thickness of the article, as well as improved production costs, when compared to an article comprising a multi-layer absorbent core.

The article can also distribute viscous fluids more efficiently to desired locations in an absorbent article, as well as provide a drier body-facing surface, and in particular configurations, can provide visual cues of absorbency. Other examples can provide improved appearance and aesthetics. As a result, an article incorporating the invention can provide greater comfort and fit, and can improve protection and increase confidence.

The cover 26 of an absorbent article 50 which includes the unitary absorbent core 30 of the present invention may include a layer constructed of any operative material, and may be a composite material. For example, the cover layer can include a woven fabric, a nonwoven fabric, a polymer film, a film-fabric laminate or the like, as well as combinations thereof. Examples of a nonwoven fabric include spunbond fabric, meltblown fabric, coform fabric, carded web, bonded carded web, bicomponent spunbond fabric or the like as well as combinations thereof. For example, the cover layer can include a woven fabric, a nonwoven fabric, a polymeric film that has been configured to be operatively liquid-permeable, or the like, as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, biodegradable aliphatic polyesters such as poly(hydroxyl alkanoates) and polyactic acid, finely perforated film webs, net materials, and the like, as well as combinations thereof.

A more particular example of a suitable cover layer material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the cover layer 26 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article (e.g., the unitary absorbent core 30). The selected arrangement of liquid-permeability is suitably present at least on an operative portion of the cover layer that is appointed for placement on the body-side of the article. The cover layer 26 can provide comfort and conformability, and can function to direct viscous fluids, such as menses, away from the body and toward the unitary absorbent core 30. In one example, the cover layer 26 can be configured to retain little or no liquid in its structure, and can be configured to provide a relatively comfortable and non-irritating surface next to the body-tissues of a female wearer. The cover layer 26 can be constructed of any material which is also easily penetrated by viscous fluids that contact the surface of the cover layer.

The cover 26 can have at least a portion of its bodyside surface treated with a surfactant to render the cover more hydrophilic. The surfactant can permit arriving viscous liquids to more readily penetrate the cover layer. The surfactant may also diminish the likelihood that the arriving viscous fluids, such as menses, will flow off the cover layer rather than penetrate through the cover layer into other components of the article. In one example, the surfactant can be substantially evenly distributed across at least a portion of the upper, bodyside surface of the cover 26 that overlays the body-facing surface 14 of the unitary absorbent core 30.

The cover 26 may be maintained in secured relation with the unitary absorbent core 30 of the present invention by bonding all or a portion of the adjacent surfaces to one another. A variety of bonding techniques known to one of skill in the art may be utilized to achieve any such secured relation. Examples of such techniques include, but are not limited to, the application of adhesives in a variety of patterns between the two adjoining surfaces, entangling at least portions of the adjacent surface of the absorbent core 30 with portions of the adjacent surface of the cover 26, co-aperturing or fusing at least portions of the adjacent surface of the cover 26 to portions of the adjacent surface of the absorbent core 30.

The cover 26 typically extends over the body-facing surface 14 of the unitary absorbent core 30, but can alternatively extend around the article to partially, or entirely, surround or enclose the core. Alternatively, the cover 26 and the baffle 28 can have peripheral margins which extend outwardly beyond the terminal, peripheral edges of the unitary absorbent core 30, and the extending margins can be joined together to partially, or entirely, surround or enclose the core.

The baffle 28 may include a layer constructed of any operative material, and may or may not have a selected level of liquid-permeability or liquid-impermeability, as desired. In one example, the backsheet or baffle 28 may be configured to provide an operatively liquid-impermeable baffle structure. The baffle 28 may, for example, include a polymeric film, a woven fabric, a nonwoven fabric or the like, as well as combinations or composites thereof. For example, the baffle 28 may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Suitably, the baffle 28 can operatively permit a sufficient passage of air and moisture vapor out of the article, particularly out of the unitary absorbent core 30, while blocking the passage of bodily liquids. An example of a suitable baffle material can include a breathable, microporous film, such as a HANJIN Breathable Baffle available from Hanjin Printing, Hanjin P&C Company Limited, a business having offices located in Sahvon-Ii.Jungan-mvu.Kongiu-City, Chung cheong nam-do, Republic of South Korea. This baffle material is a breathable film, which is white in color, dimple embossed, and contains: 47.78% calcium carbonate, 2.22% TiO2, and 50% polyethylene.

In one example, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable baffle material can include a closed-cell polyolefin foam. For example, a closed-cell polyethylene foam may be employed. Still another example of a baffle material would be a material that is similar to a polyethylene film which is used on commercially sold KOTEX brand pantiliners, and is obtainable from Pliant Corporation, a business having offices located in Schaumburg, Ill., USA.

The unitary absorbent core 30 can be sized and placed to more effectively operate in a target area of the absorbent article 50 where liquids are more likely to be introduced into the article. The structure of the unitary absorbent core 30 can be operatively configured to provide a desired level of absorbency or storage capacity. Additionally, the unitary absorbent core 30 may include one or more components that can modify the composition or rheological properties of such viscous fluids.

EXAMPLES

The unitary absorbent core 30 of the present invention exhibits similar or improved intake properties, rewet performance, saturation and retention capacity, horizontal wicking, and desorption when compared to the two-layer core (previously described), as demonstrated by the following Examples and Tables.

Several examples of the invention were prepared. The general method of preparation of the invention samples was consistent for all examples. The nonwoven layer used for the samples was an airlaid consisting of 90-percent NF 405 available from Weyerhaeuser Company, a business having offices located in Federal Way, Wash., U.S.A. and 10-percent bicomponent binder fiber T-255 available from KoSa, a business having offices located in Houston, Tex., U.S.A. Each nonwoven sample had a density of about 0.06 g/cc and a basis weight of either about 175 gsm or about 200 gsm, according to the tables below.

The samples were cut to dimensions of 13.25 inches by 2.25 inches for the 175 gsm sample and 13.25 inches by 3.125 inches for the 200 gsm sample. The samples were placed onto a screen in groups of four, and in turn were laid on a platform within a spray booth having a UNIJET spray nozzle tip TP-8001-E-SS, available from Spraying Systems Company, a business having offices located in Wheaton, Ill., U.S.A. The distance between the tip and the spray bed containing the samples was 8 inches. The spray booth was utilized at 100 psi spray pressure for application of first and second binding agents to the sample.

For purposes of the Examples, the same binding agent was used as both the first and second binding agents. Several different binding agents were utilized at various add-on levels, according to the Tables below. For application of the first binding agent, the speed of the spray boom was set to apply one-third of the desired total add-on level to the nonwoven layers.

The binding agents were prepared by diluting with a proper amount of water to obtain a solution containing 20-percent solids. In the case of AIRFLEX 192, this binding agent was prepared by first adding 1-percent by weight AEROSOL OT 75-percent surfactant, available from Cytec Industries, Inc., a business having offices located in West Patterson, N.J., U.S.A. prior to the dilution step. After preparation, the desired first binding agent was placed into the spray booth reservoir, and one spray boom pass was made.

The samples were then removed from the spray booth for application of superabsorbent material. The superabsorbent material for all samples was SXM 9394, available from Stockhausen Inc., a business having offices located in Greensboro, N.C., U.S.A. Prior to application, the superabsorbent material was sieved to obtain particles that were less than 600 microns. A desired amount of the sieved superabsorbent (according to the tables below) was then sprinkled by hand onto the first binding agent impregnated surface of the nonwoven layers while the first binding agent was still tacky. The four samples were placed on a table, a 24-pound basis weight sheet of TEKKOTE 24 KSA peel release paper, available from Tekkote Corporation, a division of American Business Products, a business having offices located in Moonachie, N.J., U.S.A. was placed on top of them, and a hollow roller made of brass weighing 28.5 pounds and measuring 4 inches in diameter, 7.25 inches in length, and having two chrome-plated handles of 4 inches each was passed over the samples one time.

The samples were then placed back into the spray booth, and two more spray boom passes were made to apply the final two-thirds of total add-on level of binding agent. The samples were then removed once again from the spray booth and placed into a model LTV Werner Mathis Through-Air-Dryer. The potentiometer was set to '5' to attain an air flow of 353.1 cfm and the temperature was set at 150 degrees Celsius. The samples were then dried for 5 minutes. The specimens were removed from the oven and allowed to air cool to room temp. The samples were then ready for storage or testing.

Table I and Table II summarize several examples of the invention, unless otherwise designated. It is contemplated that other various combinations of the identified constituents and quantities could be produced without departing from the scope of the invention.

TABLE I

| Code | Nonwoven Layer Basis Weight | 1$^{st}$ Binding Agent and Add-On Level | Superabsorbent Material and Add-On Level | 2$^{nd}$ Binding Agent and Add-On Level |
|---|---|---|---|---|
| 1 | 175 gsm | AIRFLEX 192 10 gsm | SXM 9394 30 gsm | AIRFLEX 192 20 gsm |
| 2 | 175 gsm | DUR-O-SET ELITE ULTRA 25-135A 10 gsm | SXM 9394 30 gsm | DUR-O-SET ELITE ULTRA 25-135A 20 gsm |
| 3 | 175 gsm | DUR-O-SET ELITE 33 10 gsm | SXM 9394 30 gsm | DUR-O-SET ELITE 33 20 gsm |
| 4 | 175 gsm | AIRFLEX 192 20 gsm | SXM 9394 60 gsm | AIRFLEX 192 40 gsm |
| 5 | 175 gsm | AIRFLEX 192 20 gsm | SXM 9394 90 gsm | AIRFLEX 192 40 gsm |
| 6 Non-working Example | 175 gsm | RHOPLEX B-15R 20 gsm | SXM 9394 90 gsm | RHOPLEX B-15R 40 gsm |
| 7 (Current KOTEX Two-Layer Core **) | colspan | Top Layer (body-facing side) WEYERHAEUSER NF401 semi-treated woodpulp fluff (90%); KoSa T255 bicomponent binder fiber (10%), 175 gsm, 0.06 g/cc Bottom Layer (garment-facing side) 15% by weight STOCKHAUSEN FAVOR 9543 SAP, 76.5% Weyerhaeuser NB416 untreated woodpulp fluff fiber, and 8.5% KoSa T255 bicomponent binder fiber, 225 gsm, 0.12 g/cc | | |

TABLE II

| Code | Nonwoven Layer Basis Weight | 1$^{st}$ Binding agent and Add-On Level | Superabsorbent Material and Add-On Level | 2$^{nd}$ Binding Agent and Add-On Level |
|---|---|---|---|---|
| A | 200 gsm | AIRFLEX 192 10 gsm | SXM 9394 60 gsm | AIRFLEX 192 20 gsm |
| B | 200 gsm | AIRFLEX 192 10 gsm | SXM 9394 75 gsm | AIRFLEX 192 20 gsm |

TABLE II-continued

| Code | Nonwoven Layer Basis Weight | 1st Binding agent and Add-On Level | Superabsorbent Material and Add-On Level | 2nd Binding Agent and Add-On Level |
|---|---|---|---|---|
| C | 200 gsm | DUR-O-SET ELITE ULTRA 25-135A 10 gsm | SXM 9394 60 gsm | DUR-O-SET ELITE ULTRA 25-135A 20 gsm |
| D | 200 gsm | DUR-O-SET ELITE ULTRA 25-135A 10 gsm | SXM 9394 75 gsm | DUR-O-SET ELITE ULTRA 25-135A 20 gsm |
| E | 200 gsm | DUR-O-SET ELITE 33 10 gsm | SXM 9394 60 gsm | DUR-O-SET ELITE 33 20 gsm |
| F | 200 gsm | DUR-O-SET ELITE 33 10 gsm | SXM 9394 75 gsm | DUR-O-SET ELITE 33 20 gsm |
| G (Current KOTEX Two-Layer Core **) | colspan Top Layer (body-facing side) WEYERHAEUSER NF401 semi-treated woodpulp fluff (90%); KoSa T255 bicomponent binder fiber (10%), 175 gsm, 0.06 g/cc Bottom Layer (garment-facing side) 15% by weight STOCKHAUSEN FAVOR 9543 SAP, 76.5% Weyerhaeuser NB416 untreated woodpulp fluff fiber, and 8.5% KoSa T255 bicomponent binder fiber, 225 gsm, 0.12 g/cc | | | |

** This is the current two-layer core commercially available in KOTEX ULTRATHIN MAXI sanitary pads, available from Kimberly-Clark Corporation, a business having offices located in Neenah, Wisconsin, U.S.A. As used herein, the term "semi-treated" means a debonding agent that has been employed to treat woodpulp fibers to improve opening and fiberization.WEYERHAEUSER NF401 semi-treated fluff pulp is available from Weyerhaeuser, a business having offices located in Federal Way, Washington, U.S.A. KoSa 7255 bicomponent binder fiber is available from KoSA, a business having offices located in Houston, Texas, U.S.A. The two-layer core is not an embodiment of the invention.

Examples of the invention were then tested and compared to the two-layer core for various absorbent properties using the appropriate menses simulant according to the test procedures described below. Where appropriate for test purposes, these examples were covered with a 0.5 osy spunbond composed of polypropylene and treated with 0.45-percent AHCOVEL surfactant, available from Uniqema, a division of ICI Group, a business having offices located in New Castle, Del., U.S.A. The following Table III describes the results.

TABLE III

| Code | Intake Time 1st Insult (sec.) | Intake Time 2nd Insult (sec.) | Intake Time 3rd Insult (sec.) | Rewet (g) | Desorption (%) | Horizontal Wicking Distance (cm) | Saturation Capacity (g/g) | Retention Capacity (g/g) |
|---|---|---|---|---|---|---|---|---|
| 7* | 13.5 | 41.8 | 105.9 | .93 | 51.4 | 5.0 | 10.7 | 3.1 |
| 1 | | | | | | 9.5 | | |
| 2 | | | | | | 8.8 | | |
| 3 | | | | | | 8.4 | | |
| 5 | 13.8 | 48.0 | 113.5 | 1.06 | 48.1 | | 9.2 | 3.4 |
| 6 | 20.5 | 79.4 | 230.5 | | | | | |
| A | 7.3 | 14.2 | 34.7 | 0.76 | 50.3 | | 12.1 | 3.6 |
| B | 10.5 | 17.3 | 37.4 | 0.81 | 51.0 | | 10.9 | 4.0 |
| C | 8.1 | 15.4 | 35.9 | 0.84 | 50.0 | | 11.6 | 3.9 |
| D | 8.9 | 17.5 | 39.3 | 0.83 | 50.0 | | 11.7 | 4.5 |
| E | 8.6 | 17.2 | 38.6 | 0.88 | 49.7 | | 11.5 | 3.5 |
| F | 8.0 | 16.8 | 37.3 | 0.85 | 50.3 | | 11.5 | 3.9 |
| G* | 9.1 | 20.7 | 48.9 | 0.78 | 51.4 | | 10.7 | 3.1 |

*Although Code 7 and Code G are both examples of the same two-layer core, a different batch of menses simulant was used for the testing. In general, different batches of menses simulant were used for the numerical codes versus the alphabetic codes-.Therefore, the numerical codes should be grouped together for comparison, and the alphabetic codes should be grouped together for a separate comparison.

It can be seen from Table III that even with less basis weight, the unitary absorbent core of the invention exhibits comparable or improved absorbent properties when compared to the two-layer core. For example, regarding Triple Gush Intake Time, the intake time for the first insult of the two-layer core was 9.1 seconds while the invention ranged from 7.3 seconds to 10.5 seconds, the intake time for the second insult of the two-layer core was 20.7 seconds while the invention ranged from 14.2 seconds to 17.5 seconds, and the intake time for the third insult for the two-layer core was 48.9 seconds while the invention ranged from 34.7 seconds to 39.3 seconds; for Rewet the two-layer core was 0.78 grams while the invention ranged from 0.76 grams to 0.88 grams; for Desorption the two-layer core was 51.4-percent while the invention ranged from 49.7-percent to 51.0-percent; for Saturated Capacity the two-layer core was 10.7 g/g while the invention ranged from 10.9 g/g to 12.1 g/g; and for Centrifuge Retention Capacity the two-layer core was 3.1 g/g while the invention ranged from 3.5 g/g to 4.5 g/g.

Tests

Triple Gush Intake Test

Figure 7:
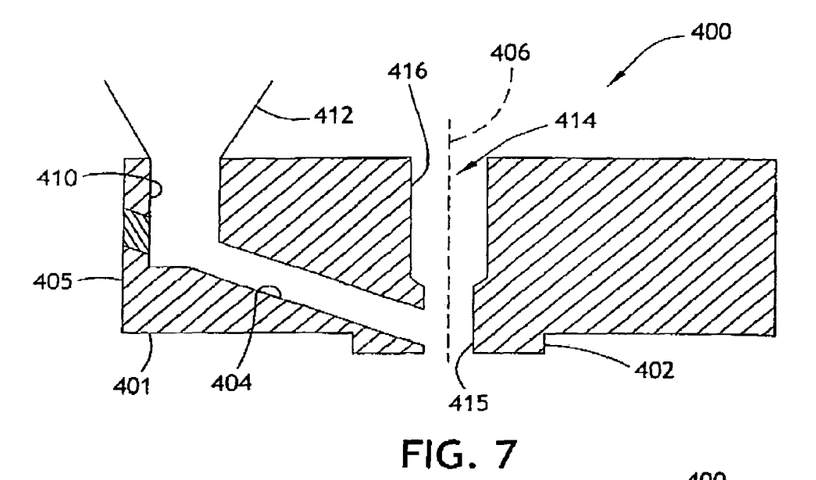
FIG. 7 shows a vertical cross-section of a rate block for conducting an Intake Test on absorbent articles.
Figure 8:
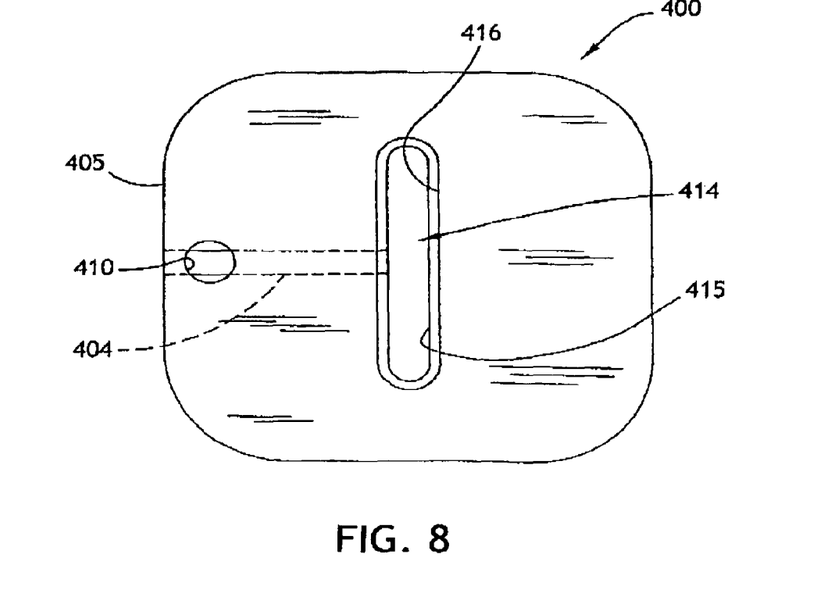
FIG. 8 shows a plan view of the rate block of FIG. 7.

This test is used to determine the intake time of a known quantity of fluid into a material and/or material system. The test apparatus consists of a clear, preferably acrylic, rate block 400, as shown in FIG. 7 and FIG. 8, and a timer or a stopwatch. A 4-inch by 4-inch piece of the unitary absorbent core and a spunbond cover material (described above) is die cut.

Take menses simulant B out of the refrigerator and mix thoroughly on a rotator for at least 30 minutes. Allow the simulant to reach room temperature. Once at room temperature, knead the bag with your hands to make sure the simulant is well mixed, and then take the hematocrit. Hematocrit should be 30%±2%.

The rate block 400 includes a central portion 402 projecting out from the bottom 401 of the block, and a channel 404 extends diagonally downward from one side 405 of the rate block to a center line 406 thereof at an angle of about 22 degrees from horizontal. The channel 404 may be made by drilling the appropriately sized hole from the side 405 of the rate block 400 at the proper angle at a point above the bottom of the rate block; provided, however, that the starting point of the drill hole in the side 405 must be subsequently plugged so that menses simulant will not escape therefrom. A top hole 410 intersects the channel 404 and is on the side 405 and sized for receiving a funnel 412 therein. A central opening 414, a 0.25 inch wide by 1.75 inches long slot, allows viewing of the progression of the menses simulant as it is taken into the absorbent structure. The central slot 414 is centered widthwise on the rate block 400 and has a bottom hole outlet 415 that is smaller in size than at the top 416 of the rate block. The top hole 410 and central slot 414 may also be formed in the rate block 400 in any suitable manner. The rate block is sized to have a predetermined weight and thus exert a preselected pressure/area (i.e. a weight of 161.9 grams will exert a pressure of 0.62 kPa over an area of 25.6 cm2.)

The rate block 400 is aligned with the long direction of the central opening 414 aligned with what would be the longitudinal direction of the absorbent structure material. The rate block 400 is then placed in the center of the sample to be tested and the sample is insulted with 2.0±0.01 ml of the menses simulant poured into the funnel 412. A stopwatch is started when the first insult reaches the test material. Once the simulant is taken completely into the sample, the stopwatch is stopped and the time on the stopwatch is recorded (e.g., in seconds) as the intake time of the first insult. The stopwatch is then reset. A timer is also started when the stopwatch is stopped and, after ten minutes have elapsed on the timer, a second insult of 2.0±0.01 ml of menses simulant is applied to the sample. The stopwatch is started to track the time needed for the sample to take in the second insult and the time is recorded as the second intake time. This procedure is repeated for the third insult also.

The Triple Gush Intake Test is conducted on five absorbent structure samples (i.e., absorbent core and cover that have been layered) and the results are averaged to obtain the intake time and rewet data for a particular absorbent structure.

Rewet Test

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and thus a dryer product. In considering rewet, three properties are important: (1) intake, if the material/system does not have good intake then fluid can rewet, (2) ability of absorbent to hold fluid (the more the absorbent holds onto the fluid the less is available for rewet), and (3) flowback, the more the absorbent system prohibits fluid from coming back through the cover, the lower the rewet.

Take simulant B out of the refrigerator and mix thoroughly on a rotator for at least 30 minutes. Allow the simulant to reach room temperature. Once at room temperature, knead the bag with your hands to make sure the simulant is well mixed, and then take the hematocrit. Hematocrit should be 30%±2%.

A 4-inch by 4-inch piece of the unitary absorbent core and a spunbond cover material (described above) is die cut. After the Triple Gush Intake Test is performed (described above), the menses simulant B is allowed to interact with the system for one minute as the rate block rests on top of the materials. The material system, cover material and absorbent, are placed onto a bag filled with fluid. A piece of blotter paper, available from Georgia-Pacific Corporation, a business having offices located in Menasha, Wis., U.S.A., is weighed and placed on top of the material system. The bag is traversed vertically until it comes into contact with an acrylic plate above it, thus pressing the whole material system against the plate blotter paper side first. The system is pressed against the acrylic plate until a total of 1 psi is applied. The pressure is held fixed for 3 minutes after which the pressure is removed and the blotter paper is weighed. The blotter paper retains any fluid that was transferred to it from the cover material/absorbent system. The difference in weight between the original blotter and the blotter after the experiment is known as the "rewet" value. Typically, 5 to 10 repetitions of this test are performed and average rewet is determined.

Centrifuge Retention Capacity and Saturation Capacity Test

Take simulant A out of the refrigerator and mix thoroughly on a rotator for at least 30 minutes. Allow the simulant to reach room temperature. Once at room temperature, knead the bag with your hands to make sure the simulant is well mixed, and then take the hematocrit. Hematocrit should be 35%±2%.

The saturation capacity and the retention capacity can be determined by soaking a 3.81 cm×3.81 cm sample of absorbent in approximately thirty milliliters of a menses simulant A in a plastic dish that is sufficient to fully saturate the sample for thirty minutes.

The pre-weighed absorbent is placed horizontally on a strip of scrim-like material (for sample handling), then placed horizontally into the thirty milliliters of test fluid making sure fluid completely covers the sample. The dish is covered so evaporation does not occur. While soaking thirty minutes, the test fluid amount is monitored so that there is always excess fluid. The sample is then removed using the scrim and placed between two pieces of approximately 4-inch by 4-inch, 2.5 osy, 0.025 g/cc bonded carded web material and on the outside of this sandwich; a layer of approximately 4-inch by 4-inch blotter paper, available from Georgia-Pacific Corporation, a business having offices located in Menasha, Wis., U.S.A., is positioned on each side such that the blotter paper is facing the outside. A pressure of 0.05 psi (0.345 kPa) is applied for five minutes to remove any pools of liquid. The saturated sample is then weighed. The weight of the liquid held in the sample divided by the dry weight of the sample is the saturation capacity of the sample.

After the saturated sample is weighed, the absorbent sample is placed in a centrifuge and spun at 300 G for three minutes so that the free fluid is discharged. The spun sample is then weighed. The weight of the liquid remaining in the spun sample divided by the dry weight of the sample is the retention capacity of the sample.

Accordingly, the saturation capacity and the retention capacity are then calculated using the following formulas:

Saturation Capacity=(Wet Wt. Before Centrifuge−Dry Wt.)/(Dry Wt.)

Retention Capacity=(Wet Wt. After Centrifuge−Dry Wt.)/(Dry Wt.)

Horizontal Wicking Test

The objective of this test is to determine the horizontal wicking capability of a material as it pulls fluid from an infinite reservoir of menses simulant fluid. The equipment and materials needed include menses simulant B, a balance readable to 0.01 grams, a sixty minute lab timer readable to one second, horizontal wicking unit, scrim bed, horizontal wicking stand, and a distance measuring device known in the art, such as a ruler, digital camera, image analysis equipment, or the like.

To determine the horizontal wicking, first cut the material to 1.5×10 inches. Take menses simulant B out of the refrigerator and mix thoroughly on a rotator for at least 30 minutes. Allow the simulant to reach room temperature. Once at room temperature, knead the bag with your hands to make sure the simulant is well mixed, and then take the hematocrit. Hematocrit should be 30%±2%. Fill the reservoir in the horizontal wicking unit with 200 milliliters of menses simulant B. Place the plug in the top of the reservoir. Remove excess simulant from the side tube of the reservoir with a syringe, and remove the air bubbles in the tubing by adjusting with the stopcock. Weigh the 1.5×10 inch test sample and record the initial weight. Measure the thickness of the sample and record the initial thickness. Fold the test sample in half lengthwise and crease. Make sure that the fluid in the reservoir is low for each sample so that the sample does not absorb until the stopcock is opened. Open the door of the x-ray unit. Place the test sample on the horizontal wicking unit with the crease in the center. Open the stopcock. When the fluid starts to wick, start the stopwatch. After one minute, measure the distance. After two minutes, take a second measurement. Repeat these steps at five-minutes, ten-minutes, twenty-minutes, and sixty-minutes. After the last measurement is taken, weigh the sample and record this as the final weight. Take the thickness at zero psi by slowly lowering the weight until it just touches the sample, and record this as the final thickness at zero psi. Let the weight slowly drop. Wait for the reading to stabilize, and record this as the final thickness at 0.05 psi.

Desorption Test

The typical object of this test is to evaluate the ability of a retention lower layer material to desorb simulant from an intake upper layer under pressure. The equipment and materials needed for this test include an electronic balance accurate to 0.001 gram, PSI loading weights for 0.3 psi, Petri dish covers, baffle, scrim, metal spatula, menses simulant B, and lab timers.

Take menses simulant B out of the refrigerator and mix thoroughly on a rotator for at least 30 minutes. Allow the simulant to reach room temperature. Once at room temperature, knead the bag with your hands to make sure the simulant is well mixed, and then take the hematocrit. Hematocrit should be 30%±2%.

To measure desorption, first prepare the materials by cutting the samples into 2 inches diameter circles. Determine the saturation capacity (described above) of the upper layer (WEYERHAEUSER NF401 semi-treated woodpulp fluff (90%); KoSa T255 bicomponent binder fiber (10%), 175 gsm, 0.06 g/cc) in menses simulant B. Record on the worksheet the upper and lower layer material names, and the amount of simulant added to the upper layer. Place a piece of baffle on the counter top. Weigh a lower layer 2 inch sample (unitary absorbent core 30 or bottom layer of a multilayer core) and record the weight on the worksheet. Place the body-facing surface of the unitary absorbent core of the present invention facing up on the baffle and then place a piece of scrim over the top. Repeat this for all five repetitions. Weigh an upper layer 2 inches sample and record the weight on the worksheet. Place the sample into a Petri dish cover. Evenly saturate the sample with the predetermined amount of simulant to 100-percent saturation. Carefully, with the metal spatula, so as not to push out any of the simulant, place the saturated sample over the scrim, directly on top of the lower layer. Place the 0.3 psi weight directly on top of the upper layer and begin the timer. Remove any excess simulant from the bottom of the Petri dish cover before beginning the next sample. Repeat for each of the five repetitions. Allow the samples to sit under pressure for 20 minutes if there is SAM in the lower layer. Then, remove the weights, remove the upper layer and discard, remove the scrim, and place the lower layer on the balance. Record the lower layer wet weight on the worksheet. Repeat for each of the five repetitions. Accordingly, the percent desorption is then calculated using the following formula:

% Desorption=(Lower Layer Wet Weight−Lower Layer Dry Weight)/Amount of Fluid Added to the Upper Layer.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:
1. A unitary absorbent core comprising:
  a single nonwoven layer having a body-facing surface and an opposing garment-facing surface;
  at least a portion of a first non-fibrous binding agent impregnated into said garment-facing surface of said nonwoven layer and wherein said body-facing surface is substantially void of said first binding agent;
  a superabsorbent material located on the garment-facing surface of said nonwoven layer in contact with said first binding agent and wherein the area between the gar- ment-facing surface and the body-facing surface of said nonwoven layer is substantially void of said superabsorbent material; and a second non-fibrous binding agent located adjacent to said superabsorbent material and superimposed on said first binding agent such that said superabsorbent material is located between said first binding agent and said second binding agent and wherein said body-facing surface of said nonwoven layer is substantially void of said second binding agent.

2. The unitary absorbent core of claim 1 wherein said nonwoven layer is airlaid.

3. The unitary absorbent core of claim 1 wherein said nonwoven layer is bonded carded web.

4. The unitary absorbent core of claim 1 wherein said nonwoven layer has a density in the range of about 0.02 g/cc to about 0.12 g/cc.

5. The unitary absorbent core of claim 1 wherein said nonwoven layer has a basis weight in the range of about 30 gsm to about 300 gsm.

6. The unitary absorbent core of claim 1 wherein said first binding agent comprises a latex binding agent.

7. The unitary absorbent core of claim 1 wherein said first binding agent comprises ethylene vinyl acetate copolymer.

8. The unitary absorbent core of claim 1 wherein said superabsorbent material is a multicomponent superabsorbent material.

9. The unitary absorbent core of claim 1 wherein said superabsorbent is present in an amount of about 5 gsm to about 150 gsm.

10. The unitary absorbent core of claim 1 wherein said superabsorbent is present in an amount of about 30 gsm to about 90 gsm.

11. The unitary absorbent core of claim 1 having a TGI Ratio, of 1.2 or less.

12. The unitary absorbent core of claim 1 wherein said second binding agent comprises a latex binding agent.

13. The unitary absorbent core of claim 1 wherein said second binding agent comprises ethylene vinyl acetate copolymer.

14. The unitary absorbent core of claim 1 comprising a total binding agent add-on level in the range of about 5 gsm to about 100 gsm.

15. The unitary absorbent core of claim 1 comprising a total binding agent add-on level in the range of about 10 gsm to about 60 gsm.

16. The unitary absorbent core of claim 1 further comprising at least one odor reducing agent.

17. The unitary absorbent core of claim 1 further comprising at least one fluid modifying agent.

18. The unitary absorbent core of claim 1 having a menses wicking distance of at least about 8 centimeters or greater as measured by a Horizontal Wicking Test.

19. The unitary absorbent core of claim 1 wherein a stain area on said body-facing surface is about 50-percent smaller than the stain area on said garment-facing surface.

20. A feminine care article having a longitudinal direction, a lateral direction, first and second longitudinally opposed end portions, and an intermediate portion located between said end portions, said article comprising:

a liquid-permeable cover;

a baffle;

a unitary absorbent core sandwiched between said cover and said baffle, said unitary absorbent core comprising a single nonwoven layer having a body-facing surface and an opposing garment-facing surface, a first non-fibrous binding agent at least partially impregnated into said garment-facing surface and wherein said body-facing surface is substantially void of said first binding agent, a superabsorbent material located on said garment-facing surface of said nonwoven layer in contact with said first binding agent and wherein the area between the garment-facing surface and the body-facing surface of said nonwoven layer is substantially void of said superabsorbent material, and a second non-fibrous binding agent located adjacent to said superabsorbent material and superimposed on said first binding agent such that said superabsorbent material is located between said first binding agent and said second binding agent and wherein said body-facing surface of said nonwoven layer is substantially void of said second binding agent.

21. The feminine care article of claim 20 wherein said garment-facing surface of said nonwoven layer is oriented towards said baffle.

22. The feminine care article of claim 20 wherein said liquid-permeable cover comprises apertures.

23. The feminine care article of claim 20 wherein said baffle is breathable.

\* \* \* \* \*